(12) United States Patent
Crockett

(10) Patent No.: US 8,117,866 B2
(45) Date of Patent: Feb. 21, 2012

(54) BODY MODIFICATION DEVICES

(76) Inventor: Derek S. Crockett, Charlotte, NC (US)

( * ) Notice: Subject to any disclaimer, the term of this patent is extended or adjusted under 35 U.S.C. 154(b) by 482 days.

(21) Appl. No.: 11/971,710

(22) Filed: Jan. 9, 2008

(65) Prior Publication Data

US 2008/0173044 A1 Jul. 24, 2008

Related U.S. Application Data

(60) Provisional application No. 60/879,412, filed on Jan. 22, 2007.

(51) Int. Cl.
*A44C 7/00* (2006.01)
*A44C 15/00* (2006.01)

(52) U.S. Cl. .................................................. 63/12; 63/13

(58) Field of Classification Search ......................... None
See application file for complete search history.

(56) References Cited

U.S. PATENT DOCUMENTS

| 4,578,063 | A | * | 3/1986 | Inman et al. | .................. 604/175 |
| 5,201,197 | A | * | 4/1993 | Bakker | ............................. 63/12 |
| 6,726,660 | B2 | * | 4/2004 | Hessel et al. | ................... 604/175 |
| 2006/0032270 | A1 | * | 2/2006 | Doyno | ........................... 63/29.1 |

* cited by examiner

*Primary Examiner* — Jack W. Lavinder
(74) *Attorney, Agent, or Firm* — Clements Bernard PLLC; Christopher L. Bernard; Lawrence A. Baratta, Jr.

(57) ABSTRACT

A body modification device including a post base, wherein the post base is configured to be disposed subcutaneously, and one or more retainer posts coupled to the post base for receiving at least one attachment.

14 Claims, 5 Drawing Sheets

BODY MODIFICATION DEVICES

CROSS-REFERENCE TO RELATED APPLICATION

This application claims the benefit of priority of U.S. Provisional Application No. 60/879,412 filed Jan. 22, 2007, and entitled "BODY MODIFICATION DEVICES" the contents of which are incorporated in full by reference herein.

FIELD OF THE INVENTION

The present invention relates generally to the body modification field. More specifically, the present invention relates to a variety of body modification devices for affixing jewels, cameras, transmission devices, or the like to the human body (including the scalp, etc.) via a non-surgical procedure. To date, no such acceptable devices or non-surgical procedures exist.

BACKGROUND OF THE INVENTION

Body modification is the permanent or semi-permanent alteration of the human body for non-medical reasons, such as spiritual or aesthetic. Transdermal and subdermal implants are two examples of body modification. A transdermal implant is the implantation of an object below the surface of the dermis, but the object exits the skin at one or more points. A subdermal implant is the implantation of an object entirely below the surface of the dermis.

Typically, the implantation of a transdermal implant is accomplished by making an incision a small distance from the site. The skin is then lifted and the implant is inserted. A hole is opened at the site for the object to pass through, and the object is positioned so that the top part of the object penetrates the hole. A portion of the implant that is inserted under the skin may contain holes, allowing the dermis to grow into the holes, thus securing the object.

The implantation of a subdermal implant involves making an incision down to the subcanteous layer in the skin. The subcutis and the fascia are separated, which creates a pocket for positioning the implant. After the implant is positioned within the pocket, the incision is sewn shut, resulting in the skin having a modified appearance.

FIGS. 1 and 2 represent the prior art in the field. FIG. 1 depicts a circular shaped post base 14 with a retainer post 12 extending therefrom. FIG. 2 depicts a post base 14 with three holes 22 positioned therein and a retainer post 12 extending from the post base 14. The holes 22 are designed to allow derma to grow therein, resulting in a more permanent modification device. The prior art device depicted in FIG. 2 is designed to be implanted into the skin on a user's head. The two front holes 22 are designed to provide increased frontal stability to prevent the device from leaning forward. These prior art devices have several disadvantages. These prior art devices are not stable when implanted, and have a tendency to migrate under the skin when implanted.

BRIEF SUMMARY OF THE INVENTION

In various exemplary embodiments, the present disclosure provides a body modification device including a post base, wherein the post base is configured to be disposed subcutaneously, and one or more retainer posts coupled to the post base.

In an exemplary embodiment of the present disclosure, the body modification device includes a post base comprising a substantially rigid portion and a substantially flexible portion.

In another exemplary embodiment of the present disclosure, the body modification device includes the post base comprising a retention member for retaining the one or more retainer posts.

In yet another exemplary embodiment of the present disclosure, the body modification device includes the post base comprising a polymeric member for stabilizing the body modification device.

In yet another exemplary embodiment of the present disclosure, the body modification device includes the polymeric member containing holes for allowing the derma to grow within for further stabilizing the body modification device.

In yet another exemplary embodiment of the present disclosure, the body modification device contains an upper threaded portion of the retainer posts for receiving a at least one attachment.

In yet another exemplary embodiment of the present disclosure, the body modification device includes the post base comprising a substantially tapering center section.

In yet another exemplary embodiment of the present disclosure, the body modification device includes the post base, wherein the post base is configured to be disposed subcutaneously, the post base comprises a polymeric member engaged to the post base for providing stability to the body modification device, and one or more retainer posts coupled to the post base, wherein the one or more retainer posts are configured to protrude from the skin of a user and receive at least one attachment.

In yet another exemplary embodiment of the present disclosure, the polymeric portion comprises spaced apart paddles.

In yet another exemplary embodiment of the present disclosure, the body modification device includes a post base, wherein the post base is configured to be disposed subcutaneously, the post base comprises a polymeric member comprising a plurality of paddles that are engaged to the post base for providing stability to the body modification device, wherein the plurality of paddles have a hold therein for providing stability to the body modification device, and one or more retainer posts coupled to the post base, wherein the one or more retainer posts are configured to protrude from the skin of a user and receive at least one attachment.

In yet another exemplary embodiment of the present disclosure, a jewel is attached to the one or more retainer posts.

In yet another exemplary embodiment of the present disclosure, a horn is attached to the one or more retainer posts.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

Figure 1:
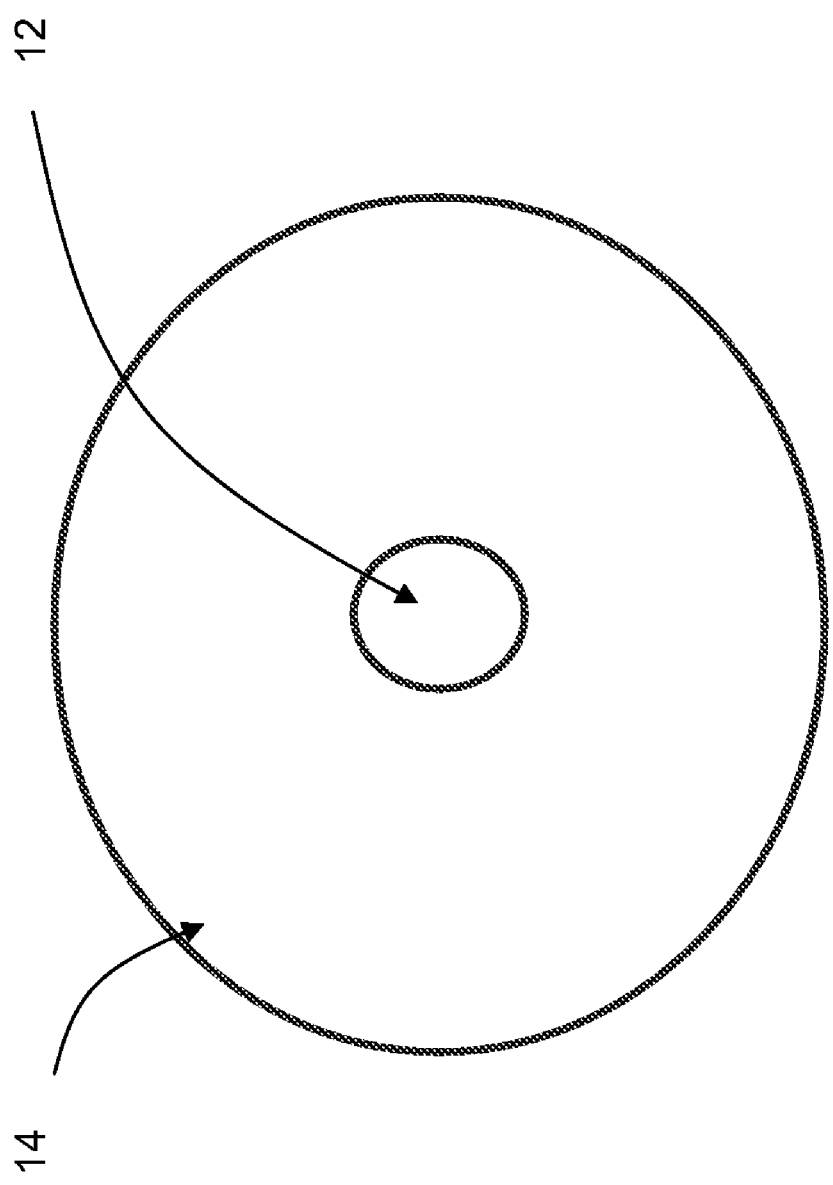
FIG. 1 is a top view of a prior art body modification device.
Figure 2:
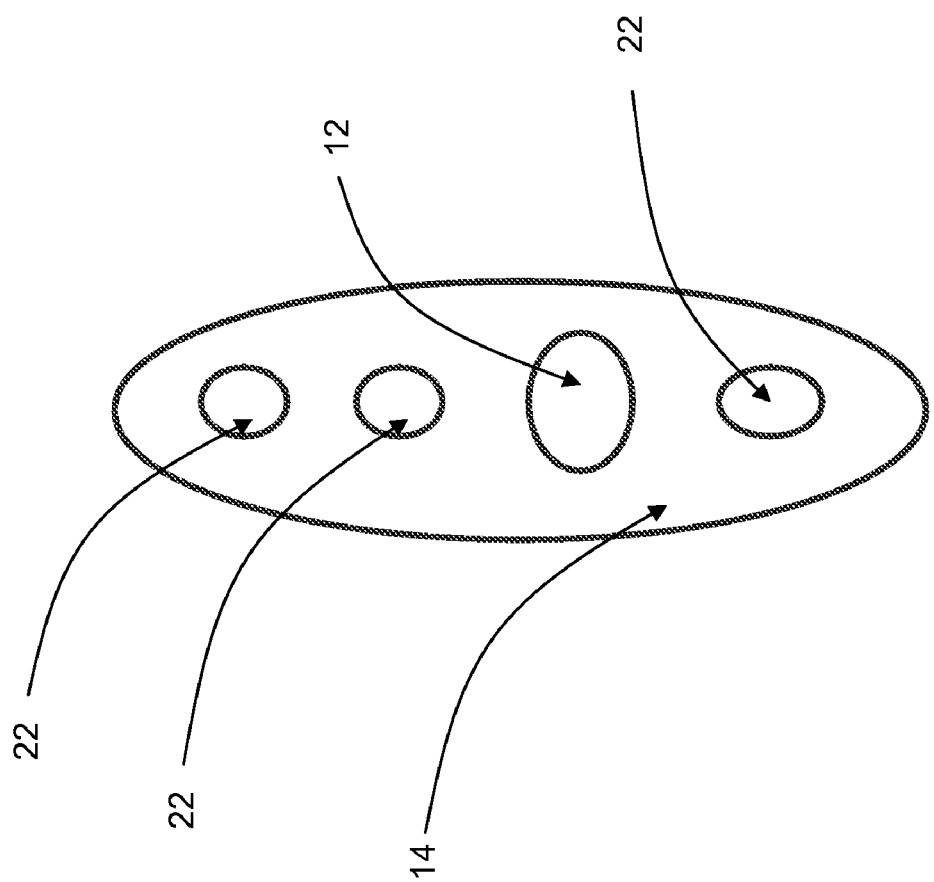
FIG. 2 is a top view of another prior art body modification device.
Figure 3:
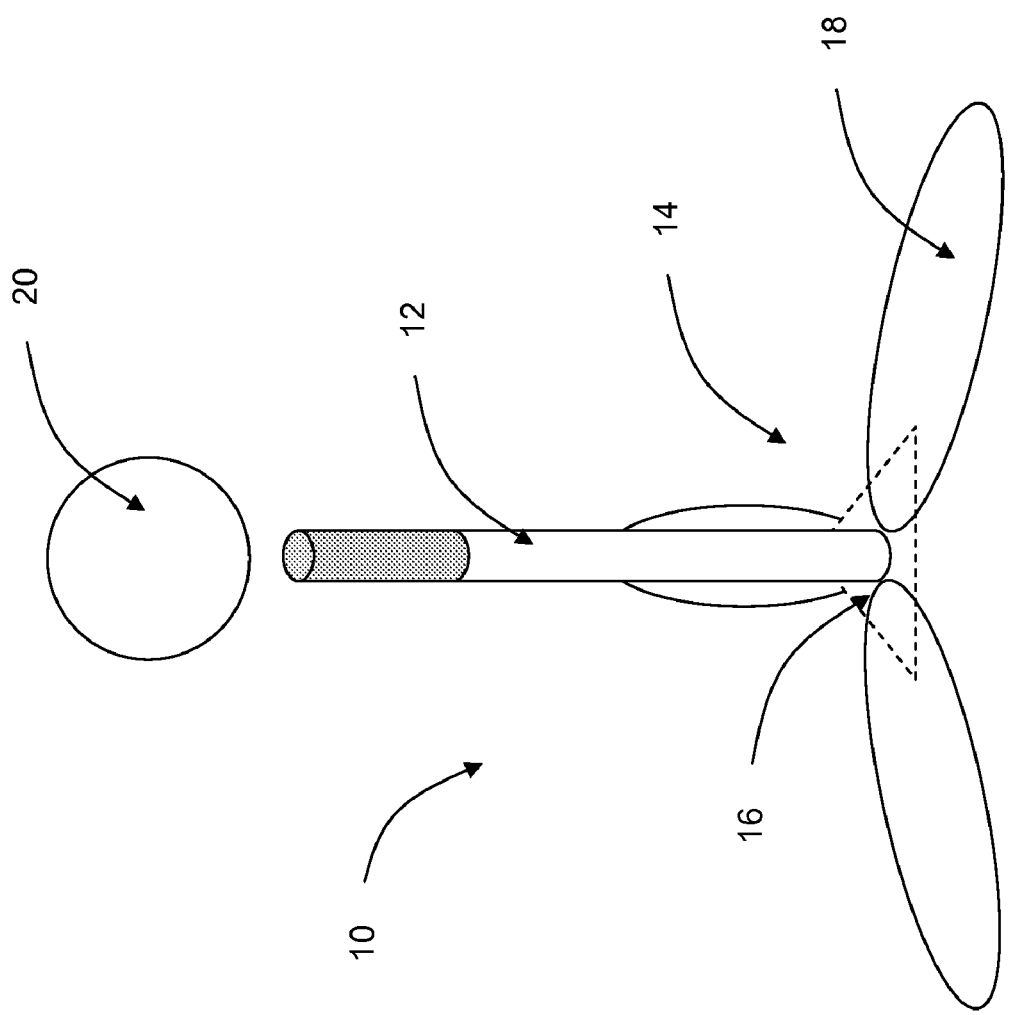
FIG. 3 is a perspective view of one illustrative embodiment of a body modification device of the present invention.

In various exemplary embodiments, referring to FIG. 3, in one illustrative embodiment, the present invention provides a body modification device 10 that includes one or more retainer posts 12 coupled to a post base 14. The post base 14 includes a retention member 16 operable for retaining the post 12 and a polymeric member 18. The retention member 16 is substantially rigid, and the polymeric member 18 is substantially flexible. The post base 14 is inserted subcutaneously, retaining the post 12 and allowing the post 12 to protrude from the skin of a user, or in the alternative, the post 12 may be used to raise the skin of a user. Optionally, the retention member 16 and polymeric member 18 are integrally formed of the same material, and the polymeric member 18 can have a three paddle design or any other comparable shape, limiting migration and rotation while holding the device 10 secure.

The retainer post 12 may be constructed of any suitable, biocompatible material, such as metal, rubber, plastic, or a combination thereof. A bottom portion of the post 12 is coupled to the retention member 16 and a top portion of the post 12 is designed to receive an attachment 20. The retainer post 12 may be of any length that is suitable for the desired uses of the user. In addition, the retainer post 12 may be of any diameter, including a plurality of varying diameters along the length of the retainer post 12.

The attachment 20 may be any device that a user desires to display atop the retainer post 12. The attachment 20 may include jewels, horns, ears, a camera, lights, reflectors, a transmission device, such as a mobile communication device, or the like. An object or sign may also be used as an attachment and attached to the retainer post 12. Alternatively, an attachment 20 may be engaged to the retainer post 12 when the body modification device 10 is implanted subdermally, creating a raised surface on the skin of the user similar to the shape of the attachment 20.

The top portion of the retainer post 12 may be threaded for receiving a correspondingly threaded bore located within an attachment 20, allowing the attachment 20 to be positioned on the retainer post 12. In another exemplary embodiment, the top portion of the post 12 may have a diameter slightly smaller than the diameter of a bore located within the attachment 20, wherein the post 12 and attachment 20 are engaged by frictional forces. In yet another exemplary embodiment, the attachment 20 is engaged to the post 12 by a male/female arrangement, wherein the post has a male end that mates with the female end of the attachment 20. In yet another exemplary embodiment, the attachment 20 has a male end that mates with the female end of the post 12.

The polymeric member 18 may be any size and shape to stabilize the body modification device 10 on the body part that the body modification device 10 is inserted. As illustrated in FIG. 3, the polymeric member 18 comprises three spaced apart paddles made of a biocompatible rubber material. The paddles are spaced an equal distance apart. Any number of paddles and any distance of spacing between the paddles may be employed. In addition, the polymeric member 18 may consist of any embodiment that effectively stabilizes the body modification device 10. For example, loops, barbs, arms, fins, or any similar shaped object may be utilized in the polymeric member 18 to stabilize the body modification device 10.

Figure 4:
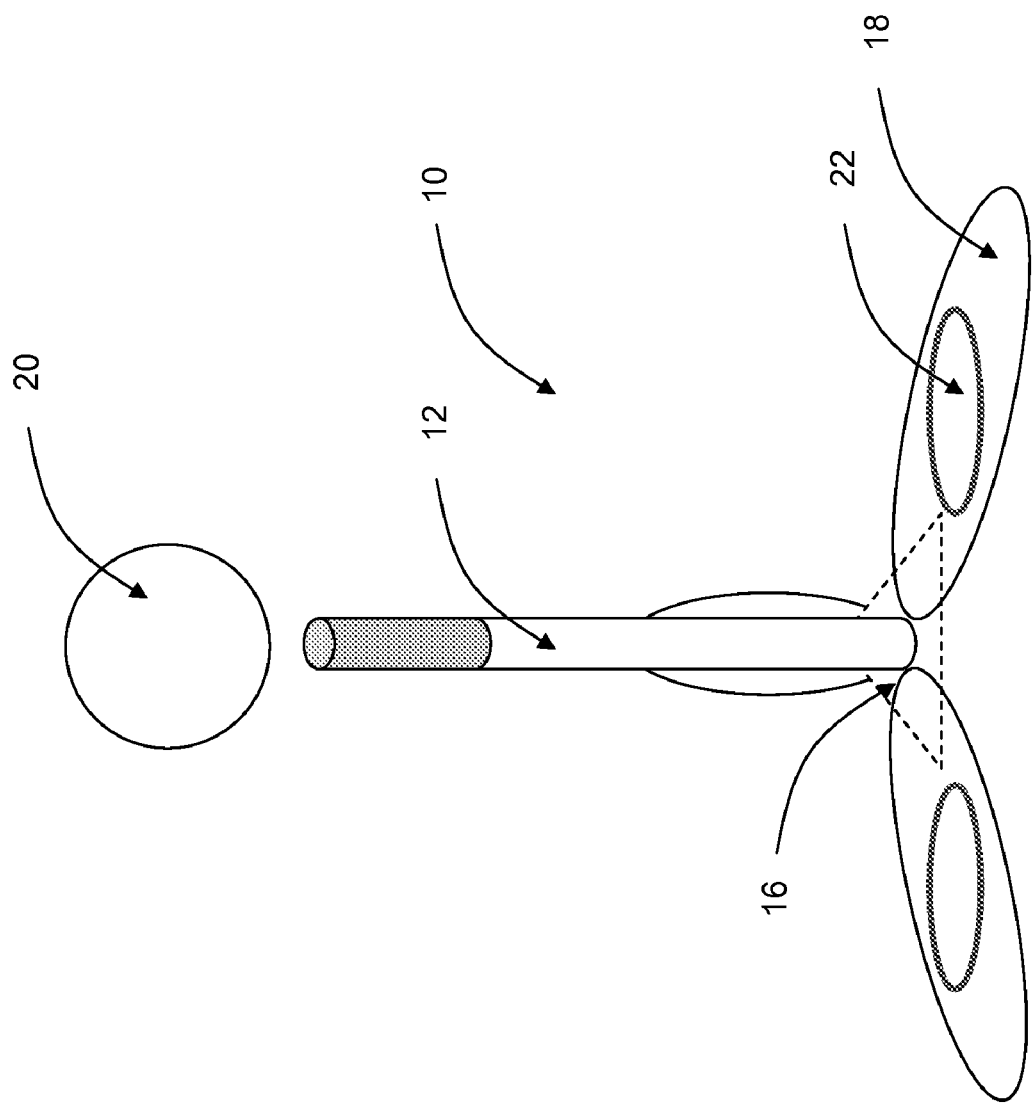
FIG. 4 is a perspective view of another illustrative embodiment of a body modification device of the present invention.

Furthermore, the paddles, or other similarly effective shape, of the polymeric member 18 may contain at least one hole 22 in at least one polymeric member 18, as shown in FIG. 4. The purpose of the hole 22 is to allow the derma to grow through the hole 22 for stabilizing the body modification device 10. Instead of a hole 22, the polymeric member 18 may contain a bore, orifice, opening, hollow, or cavity that allows derma to grow therethrough, thus further stabilizing the body modification device 10.

In operation, the post base 14, including the retention member 16 and polymeric member 18, are inserted subcutaneously. The polymeric member 18 is substantially flexible allowing the footprint of the polymeric member 18 to be constricted for insertion into the incision in the skin. Once the substantially flexible polymeric member 18 is inserted inside the incision, the polymeric member 18 may be returned to its original position. The purpose of polymeric member 18 is to stabilize the body modification device 10. The retention member 16 aids in the stability of the modification device 10 and aids in the engagement of the polymeric member 18 to the post 12. The retention member 16 is substantially rigid, aiding the stability of the modification device 10 and the engagement of the polymeric member 18 to the post 12. Alternatively, the post 12 may be engaged to the polymeric member 18 directly without the need for the retention member 16.

Figure 5:
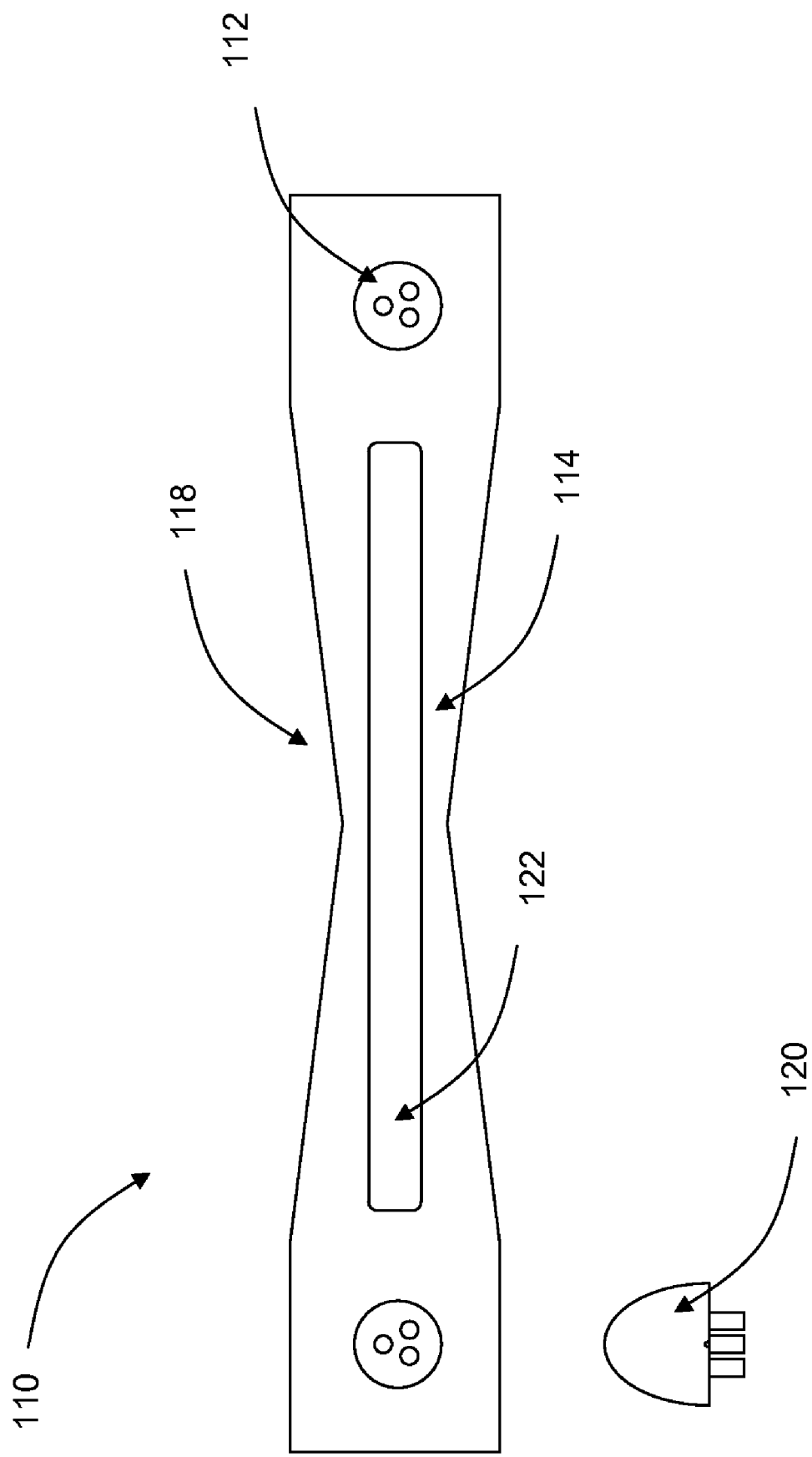
FIG. 5 is a top/side planar view of another illustrative embodiment of a body modification device of the present invention.

Referring to FIG. 5, in another illustrative embodiment, the present invention provides a body modification device 110 that includes a plurality of retainer posts 112 coupled to a post base 114. The post base 114 includes a substantially tapering center section 118. The post base 114 is inserted subcutaneously, retaining the posts 112 and causing them to protrude from the skin of a user. Optionally, a hole 122 is positioned with the post base 114, allowing derma to grow therein for providing stability to the modification device 110.

The retainer posts 112 may be constructed of any suitable material. Preferably, the retainer posts 112 may be constructed of a biocompatible metal, rubber, plastic, or a combination thereof. A bottom portion of the posts 112 is coupled to the post base 114 and a top portion of the posts 112 is designed to receive an attachment 120. The retainer posts 112 may be of any length that is suitable for the uses of the user. In addition, the retainer posts 112 may be of any diameter, including a plurality of varying diameters along the length of the retainer posts 112.

The attachment 120 may be any device that a user wants to display atop the retainer posts 112. The attachment 120 may include jewels, horns, ears, a camera, lights, reflectors, a transmission device, such as a mobile communication device, or the like. An object or sign may also be used as an attachment 120 and attached to the retainer posts 112. Alternatively, an attachment 120 may be engaged to the retainer post 112 when the body modification device 110 is implanted subdermally, creating a raised surface on the skin of the user similar to the shape of the attachment 120.

As illustrated in FIG. 5, the attachment 120 is engaged to the posts 112 by a male/female arrangement, wherein the posts 112 have a female end that mates with the male end of the attachment 120. Alternatively, the posts 112 have a male end that mates with the female end of the attachment. In another embodiment, the top portion of the posts 112 may be threaded for receiving a correspondingly threaded bore located within an attachment 120. In another exemplary embodiment, the top portion of the posts 112 has a diameter slightly smaller than the diameter of a bore located within the attachment 120, wherein the posts 112 and attachment 120 are engaged by frictional forces.

In operation, the post base 114 is inserted subcutaneously. The post base 114 lies beneath the skin and the retention posts 112 extend upward through the skin. The embodiment as illustrated in FIG. 5 allows a single post base 114 to be inserted subcutaneously while a plurality of retention posts 112 extend therefrom. The hole 122 located within the post base 114 allows derma to grow therein, thus stabilizing the modification device 110.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. A body modification device, comprising:
    a post base, wherein the post base is configured to be disposed subcutaneously, wherein the post base comprises a polymeric member for stabilizing the body modification device, and wherein the polymeric member contains holes for allowing derma to grow within for further stabilizing the body modification device;
    one or more retainer posts coupled to the post base; and
    one or more of a jewel, a horn, a light, a camera, and a mobile communication device attached to the one or more retainer posts.

2. The body modification device of claim 1, wherein the post base comprises a substantially rigid portion and a substantially flexible portion.

3. The body modification device of claim 1, wherein the post base comprises a retention member for retaining the one or more retainer posts.

4. The body modification device of claim 1, further comprising an upper threaded portion of the retainer posts for receiving at least one attachment.

5. The body modification device of claim 1, wherein the post base comprises a substantially tapered center section.

6. A body modification device, comprising:
    a post base, wherein the post base is configured to be disposed subcutaneously; wherein the post base comprises a polymeric member for providing stability to the body modification device, and wherein the polymeric member contains holes for allowing the derma to grow within for further stabilizing the body modification device; and
    one or more retainer posts coupled to the post base, wherein the one or more retainer posts are configured to protrude from the skin of a user and receive at least one attachment, wherein the at least one attachment comprises one or more of a jewel, a horn, a light, a camera, and a mobile communication device.

7. The body modification device of claim 6, wherein the post base comprises a substantially rigid portion and a substantially flexible portion.

8. The body modification device of claim 6, wherein the post base comprises a retention member for retaining the one or more retainer posts.

9. The body modification device of claim 6, further comprising an upper threaded portion of the one or more retainer posts for receiving at least one attachment.

10. The body modification device of claim 6, wherein the polymeric member comprise spaced apart paddles.

11. A body modification device, comprising:
    a post base, wherein the post base is configured to be disposed subcutaneously, wherein the post base comprises a polymeric member comprising a plurality of paddles that are engaged to the post base for providing stability to the body modification device, wherein the plurality of paddles have a hole therein for providing stability to the body modification device; and
    one or more retainer posts coupled to the post base, wherein the one or more retainer posts are configured to protrude from the skin of a user and receive at least one attachment, wherein the at least one attachment comprises one or more of a jewel, a horn, a light, a camera, and a mobile communication device.

12. The body modification device of claim 11, wherein the post base comprises a substantially rigid portion and a substantially flexible portion.

13. The body modification device of claim 11, wherein the post base comprises a retention member for retaining the one or more retainer posts.

14. The body modification device of claim 11, further comprising an upper threaded portion of the one or more retainer posts for receiving the at least one attachment.

\* \* \* \* \*